United States Patent [19]

van Staaveren

[11] Plant 4,937

[45] Nov. 9, 1982

[54] CARNATION NAMED STASALM

[75] Inventor: Maurits C. van Staaveren, 30 Hornweg, at 1432 GM, Aalsmeer, Netherlands

[73] Assignees: B. V. Handelskwekerij; van Staaveren, M. C., both of Aalsmeer, Netherlands

[21] Appl. No.: 225,332

[22] Filed: Jan. 15, 1981

[51] Int. Cl.[3] ..... A01H 5/00

[52] U.S. Cl. ..... Plt./71

[58] Field of Search ..... Plt./71

*Primary Examiner*—Robert E. Bagwill

*Attorney, Agent, or Firm*—C. W. Rummler

[57] ABSTRACT

A new variety of carnation plant distinguished by the whitish pink coloring of its medium sized blooms, which are borne on sturdy pedicels carried by long, strong peduncles and by its continuous and abundant production of flowers.

1 Drawing Figure

BACKGROUND OF THE NEW PLANT

This new carnation cultivar originated at Aalsmeer, The Netherlands, as a seedling derived by my crossing of unnamed and unpatented carnation varieties selected from breeding stock maintained for production of new varieties for the commercial market, the before mentioned crossing having been made with the object of developing a plant having a new color and better production. This new plant was observed by me to have an unusual floral coloration, as well as other desirable characteristics, and for that reason was selected for asexual propagation and testing, which was done by cuttings at Aalsmeer with favorable results. Subsequent propagation through successive generations has demonstrated that the novel characteristics of this new plant hold true from generation to generation and appear to be firmly fixed.

DESCRIPTION OF THE DRAWING

My new carnation cultivar is illustrated by the accompanying full color photographic drawing which shows the inflorescence of a fully grown plant, the view including buds in various stages of opening, as well as fully opened flowers, the color rendition being as nearly true as it is reasonably possible to obtain by means of conventional photographic procedures.

DESCRIPTION OF THE NEW PLANT

The following is a detailed description of my new carnation plant based upon observations of plants grown under conventional greenhouse procedures, the color designations being according to The R.H.S. Colour Chart published by The Royal Horticultural Society of London, England.

THE PLANT

Origin: Seedling.

Parentage:

*Seed parent.*—Pink Barbie (unpatented).

*Pollen parent.*—No. 7401-1C (unpatented). The pollen parent is maintained in greenhouse at Aalsmeer, The Netherlands, and is identified in my permanent records by the above designation.

Classification:

*Botanic.*—*Dianthus caryophyllus.*

*Commercial.*—Greenhouse carnation for cut flowers.

Form: Bush.

Height: About 120 cm.

Growth: Strong and upright.

Branching: Normal.

Foliage:

*Quantity.*—Moderate.

*Leaf size.*—Moderate. Shape: oblong.

*Texture.*—Smooth.

*Color.*—Upper side — Grey Green with waxy layer. Under side — Grey Green with waxy layer.

THE BUD

Size: Medium, about 15 mm. in diameter and about 40 mm. in length.

Form: Generally ovoid becoming cylindrical when opening.

Opening rate: Moderate.

Color:

*When sepals first divide.*—Yellow Green.

*When petals begin to unfurl.*—Yellow Green.

Sepals:

*Condition.*—Upstanding.

*Color.*—Inside — Grey Green. Outside — Yellow Green with White tips.

Calyx:

*Shape.*—Tubular.

*Size.*—Moderate, about 15 mm. broad and 30 mm. long.

*Splitting.*—Calyx does not split.

*Aspect.*—Smooth.

Peduncle: Rigid and erect.

*Color.*—Grey Green.

THE FLOWER

Blooming habit: Continuous and abundant.

Size of bloom: Medium.

*Diameter.*—About 50 mm.

*Depth.*—About 15 mm.

Borne: Singly on strong, upright pedicels.

Shape: High centered when bloom first opens. This shape does not change.

Petalage:

*Number of petals.*—About 50.

*Arrangement.*—Generally imbricated.

*Color.*—Outer petals: body — 50D–55D. Base — Light Green. Inside petals: body — 50D–55D. Reverse side: 50D–55D.

*Texture.*—Soft.

*Appearance.*—Shiny.

Peduncle: Flowering stem — sturdy and upright.

*Length.*—About 50 cm.

*Color.*—Dark Green with Blue/Grey waxy layer.

Persistence: Petals hang on and dry and the bloom stays upright.

Fragrance: Slight.

Lasting quality:

*On the plant.*—About 14 days.

*As a cut flower.*—About 8 to 10 days.

REPRODUCTIVE ORGANS

Stamens:

*Anthers.*—Many in number and of varying lengths.

*Filaments.*—Color — Cream/White.

*Pollen.*—Color — Yellow.

Pistils:

*Number.*—Not more than 3.

*Length.*—About 40 mm.

*Stigmas.*—Color — Cream/White.

Fruit: The fruit is fertile.

*Shape.*—Oblong.

*Color at maturity.*—Green-Brown.

I claim:

1. A new and distinct variety of carnation plant, substantially as herein shown and described, characterized by its whitish pink flowers borne singly on sturdy, upright pedicels carried on long, strong peduncles, and by its abundant production of blooms.

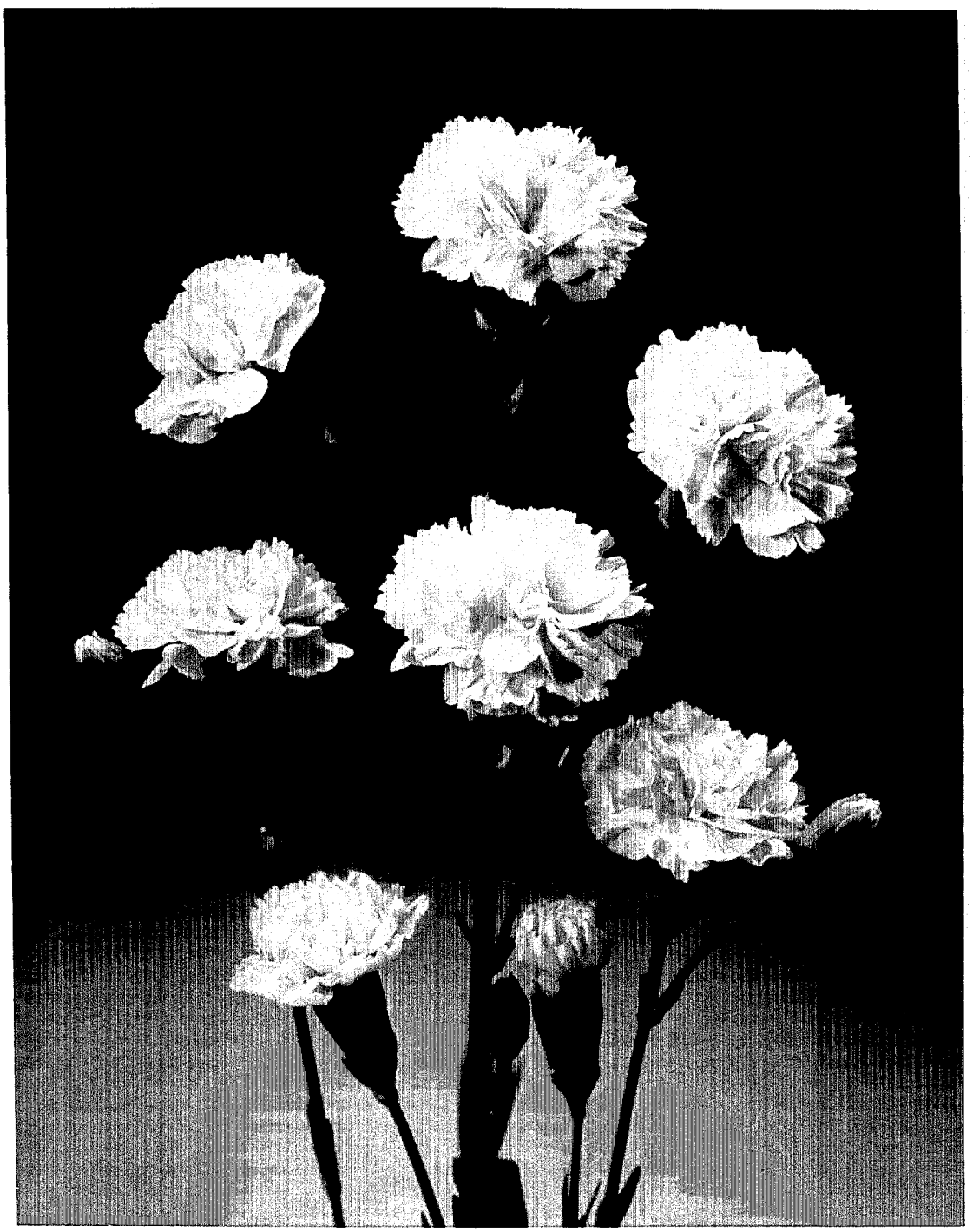

* * * * *